United States Patent
Neckers et al.

(10) Patent No.: US 9,101,601 B2
(45) Date of Patent: Aug. 11, 2015

(54) METHODS OF TREATING OR PREVENTING INSULIN RESISTANCE AND ASSOCIATED DISEASES AND CONDITIONS

(71) Applicant: The United States of America, as represented by the Secretary, Department of Health and Human Service, Washington, DC (US)

(72) Inventors: Leonard M. Neckers, Bethesda, MD (US); Carole A.C. Sourbier, Rockville, MD (US); W. Marston Linehan, North Bethesda, MD (US); Jane B. Neckers, Bethesda, MD (US); Min-Jung Lee, North Potomac, MD (US); Bradley T. Scroggins, Rockville, MD (US); John A. Beutler, Union Bridge, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/370,140

(22) PCT Filed: Jan. 3, 2013

(86) PCT No.: PCT/US2013/020051
§ 371 (c)(1),
(2) Date: Jul. 1, 2014

(87) PCT Pub. No.: WO2013/106226
PCT Pub. Date: Jul. 18, 2013

(65) Prior Publication Data
US 2014/0350093 A1 Nov. 27, 2014

Related U.S. Application Data

(60) Provisional application No. 61/584,526, filed on Jan. 9, 2012.

(51) Int. Cl.
| | |
|---|---|
| *A61K 31/352* | (2006.01) |
| *C07D 311/64* | (2006.01) |
| *A61K 31/343* | (2006.01) |
| *A61K 31/4745* | (2006.01) |
| *A61K 31/381* | (2006.01) |
| *A61K 31/382* | (2006.01) |
| *A61K 31/46* | (2006.01) |
| *C07D 311/94* | (2006.01) |

(52) U.S. Cl.
CPC ............ *A61K 31/343* (2013.01); *A61K 31/352* (2013.01); *A61K 31/381* (2013.01); *A61K 31/382* (2013.01); *A61K 31/46* (2013.01); *A61K 31/4745* (2013.01); *C07D 311/94* (2013.01)

(58) Field of Classification Search
CPC .................................................... A61K 31/352
See application file for complete search history.

(56) References Cited

U.S. PATENT DOCUMENTS

2003/0186941 A1  10/2003  Roberts et al.
2010/0286259 A1*  11/2010  Beutler et al. ................ 514/468
2011/0112073 A1  5/2011  Thiele et al.

FOREIGN PATENT DOCUMENTS

WO  WO 00/56341 A1  9/2000
WO  WO 2011/120886 A1  10/2011
WO  WO 2013/106226 A2  7/2013

OTHER PUBLICATIONS

Sourbier et al. (abstract 959: Targeting renal cell carcinoma with englerin A- Cancer Res., Apr. 15, 2011, vol. 71; 959).*
Kavanagh et al., "Restoring HSP70 deficiencies improves glucose tolerance in diabetic monkeys," *Am. J. Physiol. Endocrinol. Metab.*, 300 (5), E894-E901 (2011).

* cited by examiner

*Primary Examiner* — Valerie Rodriguez-Garcia
(74) *Attorney, Agent, or Firm* — Leydig, Voit & Mayer, Ltd.

(57) ABSTRACT

Disclosed are methods of treating an animal for insulin resistance and associated diseases or conditions, activating the transcriptional activity of heat shock factor 1 (HSF1), or inducing the expression of heat shock protein 70 (HSP70) in an animal in need thereof, wherein the methods involve administering an effective amount of one or more compounds of formula (I) or an epimer thereof, wherein Ar, and $R^1$-$R^6$ are described herein. Examples of diseases or conditions associated with insulin resistance include diabetes, obesity, inflammation, metabolic syndrome, polycystic ovary disease, arteriosclerosis, non-alcoholic fatty liver disease, reproductive abnormality in a female, and growth abnormality.

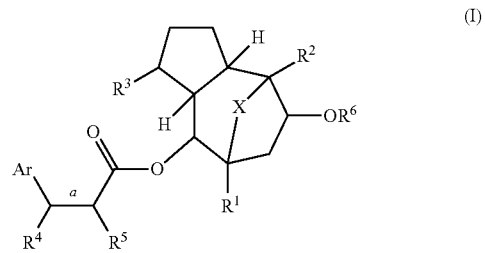

13 Claims, 2 Drawing Sheets

METHODS OF TREATING OR PREVENTING INSULIN RESISTANCE AND ASSOCIATED DISEASES AND CONDITIONS

CROSS-REFERENCE TO A RELATED APPLICATION

This patent application is the U.S. national phase of International patent application No. PCT/US2013/020051, filed Jan. 3, 2013, which claims the benefit of U.S. Provisional Patent Application No. 61/584,526, filed Jan. 9, 2012, which are incorporated by reference.

BACKGROUND OF THE INVENTION

A common problem faced by patients suffering from type 2 diabetes or obesity is the development of insulin resistance. Insulin resistance is characterized by impaired uptake and utilization of glucose in insulin sensitive target organs such as adipocytes and skeletal muscle, and impaired inhibition of hepatic glucose output. The functional insulin deficiency and the failure of insulin to suppress hepatic glucose output results in fasting hyperglycemia. Pancreatic β-cells compensate, at first, for the insulin resistance by secreting increased levels of insulin. However, the β-cells are unable to maintain the high output of insulin and eventually the glucose-induced insulin secretion falls, leading to the deterioration of glucose homeostasis and to subsequent development of overt diabetes. Majority of patients with type 2 diabetes are obese.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with type 2 diabetes have a significantly increased risk of macrovascular and microvascular complications, including atherosclerosis, coronary heart disease, stroke, peripheral vascular disease, hypertension, fatty liver, reproductive abnormalities in women, growth abnormalities, nephropathy, neuropathy, and retinopathy.

Diabetes currently affects approximately 170 million people worldwide with the World Health Organization (WHO) predicting 300 million diabetics by 2025. The United States alone has 20.8 million people suffering from diabetes (approximately 6% of population and the $6^{th}$ most common cause of death). The annual direct healthcare costs of Diabetes worldwide for people in the 20-79 age bracket are estimated at $153-286 billion and is expected to rise to $213-396 billion in 2025.

While there are many drugs on the market for treating insulin resistance and associated diseases and conditions, there still exists a need for therapeutic agents for treating and/or preventing insulin resistance and associated diseases and conditions.

BRIEF SUMMARY OF THE INVENTION

The present invention is predicated, at least in part, on the surprising discovery that englerin A, a compound for use in an embodiment of the invention, when administered to mice with tumor, displayed significantly lower blood glucose levels than a control group of mice with tumor but not treated with englerin A. It was further observed that mice treated with englerin A displayed increased expression of HSP70 compared with vehicle treated mice. HSP70 is a marker of cell stress and is transcribed by the heat shock factor 1 (HSF1). It was also observed that englerin A significantly activates HSF1, its transcriptional activity, in a PKCθ dose dependent manner. Since PKCθ activation has been related to inducement of insulin resistance, it is believed that activation of HSP70 counteracts the insulin resistance induced by PKCθ activation.

Accordingly, the present invention provides methods of treating or preventing insulin resistance and associated diseases or conditions, activating the transcriptional activity of heat shock factor 1 (HSF1) or inducing the expression of heat shock protein 70 (HSP70) in an animal in need thereof, wherein the methods involve administering one or more compounds of formula (I), salts thereof, or epimers thereof, as described herein.

DETAILED DESCRIPTION OF THE INVENTION

An aspect of the present invention involves activation of the heat shock protein 70 (HSP70). Heat shock proteins (HSPs) are the largest family of transcriptionally regulated molecular chaperone proteins that respond to cellular stress. HSPs aid in repair of protein damage and survival of normal cellular functions. Insulin resistance and hyperglycemic people have reduced HSP70 protein and gene expression. HSP70 assists in protein folding and re-folding. Heat shock factor 1 (HSF1) mediates most transcriptional activation by binding to heat shock elements in the promoter region of the HSP genes, with the resultant transcription of HSP70 mRNA being most abundant. In resting cells, HSF1 is complexed with various heat shock proteins such as HSP70 and/or HSP90. After stress, damaged proteins become abundant and liberate the heat shock factor from its HSP70 or HSP90 complex. This process sets the stage for the trimerization, nuclear translocation and phosphorylation of HSF1, which are all prerequisites for its binding the special nucleotide segments, called heat shock elements in the promoter region of the HSP genes. HSF1 thus undergoes modifications such as trimerization, phosphorylation, and acetylation as well as product feedback inhibition to modulate the activation-attenuation cycle.

Induction of HSPs not only protects de novo proteins being translated through the endoplasmic reticulum but also protects oxidized proteins and upregulates intracellular antioxidant mechanisms, which together minimize the chronic inflammatory state associated with insulin resistance. See, for example, Kavanagh, K., et al. *Am. J Physiol Endocrinol Metab.* 300: E894-E901, 2011, which also shows that restoring HSP70 deficiencies improves glucose tolerance in diabetic monkeys. HSP70 is also known to prevent damage to cardiac muscle by both ischemia and reperfusion. Curie et al., Heat-shock response is associated with enhanced postischemic ventricular recovery, *Cir. Res.* 63, 395-397 (1988). Aged organisms contain an increased amount of misfolded proteins, and the induction of HSP70 is impaired in both aged rats and humans. Induction of heat shock proteins also leads to increased life expectancy in yeast, *Drosophila* or *C. elegans*.

Accordingly, in accordance with an embodiment, the invention provides a method of treating an animal for a disease or condition associated with insulin resistance comprising administering to the animal an effective amount of a compound of formula (I):

or an epimer thereof; wherein

Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;

X is O, NH, or S;

$R^2$ and $R^3$ are independently $C_1$-$C_6$ alkyl;

$R^1$ is isopropyl or isopropylenyl;

"a" is a single bond or a double bond;

when "a" is a double bond, $R^4$ is hydrogen, and $R^5$ is halo or H;

when "a" is a single bond, $R^4$ is selected from the group consisting of halo, hydroxy, and $C_1$-$C_6$ alkoxy and $R^5$ is halo or H; and $R^6$ is H, $C_1$-$C_6$ alkyl carbonyl, or hydroxy $C_1$-$C_6$ alkyl carbonyl.

In accordance with another embodiment, the invention provides a method of activating transcriptional activity of heat shock factor 1 (HSF1) or inducing the expression of heat shock protein 70 (HSP70) in an animal in need thereof comprising administering to the animal an effective amount of a compound of formula (I):

or an epimer thereof; wherein

Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;

X is O, NH, or S;

$R^2$ and $R^3$ are independently a $C_1$-$C_6$ alkyl;

$R^1$ is isopropyl or isopropylenyl;

"a" is a single bond or a double bond;

when "a" is a double bond, $R^4$ is hydrogen, and $R^5$ is halo or H;

when "a" is a single bond, $R^4$ is selected from the group consisting of halo, hydroxy, and $C_1$-$C_6$ alkoxy and $R^5$ is halo or H; and $R^6$ is H, $C_1$-$C_6$ alkyl carbonyl, or hydroxy $C_1$-$C_6$ alkyl carbonyl.

In an embodiment, the invention provides a compound formula (I):

or an epimer thereof; wherein

Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;

X is O, NH, or S;

$R^2$ and $R^3$ are independently $C_1$-$C_6$ alkyl;

$R^1$ is isopropyl or isopropylenyl;

"a" is a single bond or a double bond;

when "a" is a double bond, $R^4$ is hydrogen, and $R^5$ is halo or H;

when "a" is a single bond, $R^4$ is selected from the group consisting of halo, hydroxy, and $C_1$-$C_6$ alkoxy and $R^5$ is halo or H; and $R^6$ is H, $C_1$-$C_6$ alkyl carbonyl, or hydroxy $C_1$-$C_6$ alkyl carbonyl; for use in treating an animal for a disease or condition associated with insulin resistance or for use in activating transcriptional activity of heat shock factor 1 (HSF1) or inducing the expression of heat shock protein 70 (HSP70) in an animal in need thereof.

In accordance with any of the embodiments of the invention, the term "aryl" refers to a mono, bi, or tricyclic carbocyclic ring system having one, two, or three aromatic rings, for example, phenyl, naphthyl, anthracenyl, or biphenyl. The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise 4n+2π electrons, according to Hückel's Rule, wherein n=1, 2, or 3.

Whenever a range of the number of atoms in a structure is indicated (e.g., a $C_{1-6}$ or $C_{14}$ alkyl, alkoxy, hydroxyalkyl, etc.), it is specifically contemplated that any sub-range or individual number of carbon atoms falling within the indicated range also can be used. Thus, for instance, the recitation of a range of 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, and/or 6 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 2-3 carbon atoms, 2-4 carbon atoms, 2-5 carbon atoms, 2-6 carbon atoms, 3-4 carbon atoms, 3-5 carbon atoms, 3-6 carbon atoms, 4-5 carbon atoms, and 4-6 carbon atoms, as appropriate).

In any of the above embodiments of the invention, $R^6$ is hydroxy $C_1$-$C_6$ alkyl carbonyl, particularly $C_1$-$C_3$ hydroxyalkyl carbonyl, and more particularly hydroxymethyl carbonyl.

In accordance with any of the embodiments, $R^5$ is halo, i.e., fluoro, chloro, bromo, or iodo, particularly chloro.

In any of the embodiments of the invention, Ar is phenyl, naphthyl, or anthracenyl, optionally substituted with $C_1$-$C_6$ alkyl, $C_1$-$C_6$ hydroxyalkyl, $C_1$-$C_6$ alkoxy, halo, or nitro. In a particular embodiment, Ar is phenyl, optionally substituted with $C_1$-$C_6$ alkyl, $C_1$-$C_6$ hydroxyalkyl, $C_1$-$C_6$ alkoxy, halo, or nitro.

In any of the embodiments of the invention, X is preferably O.

In any of the embodiments of the invention, $R^1$ is particularly isopropyl.

In any of the embodiments of the invention, "a" is a double bond or single bond. When "a" is a double bond, the double bond can be E, Z, or a mixture of E and Z (i.e., E/Z). In embodiments where "a" is a single bond, $R^4$ is hydroxy, chloro, or ethoxy.

In another embodiment, the invention provides methods wherein, in the compound of formula (I) or epimer thereof, $R^6$ is $C_1$-$C_6$ alkylcarbonyl, particularly, $C_1$-$C_3$ alkylcarbonyl.

In any of the embodiments, in the compound of formula (I) or epimer thereof, $R^2$ and $R^3$ are particularly methyl.

Specific examples of the compound of formula (I) for use in any of the above embodiments are:

2'-Chloroenglerin A

2'-Chloro,3'-hydroxydihydroenglerin A (epimer 1, 2, 3, or 4)

2',3'-Dichlorodihydroenglerin A (epimer 1 or 2)

2'-Chloro,3'-ethoxydihydroenglerin A wherein the double bond "a" in 2'-Chloroenglerin A can be E, Z, or a mixture of E and Z. 2'-chloro,3'-hydroxydihydroenglerin A (epimers 1-4) have the same planar structure but are epimers of one another. 2',3'-dichlorodihydroenglerin A (epimers 1 and 2) have the same planar structure but are epimers of each other.

In a specific embodiment of the above methods, the compound of formula (I) is Englerin A, which is of the formula:

and more specifically, (−)-Englerin A:

The compounds above can be isolated or purified from natural sources, for example, from the root bark and stem bark of the plant *Phyllanthus engleri* Pax (Euphorbiaceae). This species has a long history as a toxic plant. The book "Common Poisonous Plants of East Africa" (B. Verdcourt & E. C. Trump, 1969) reports that the root and bark of this plant are toxic and lethal when smoked. This property has been used for committing suicide. Experimental work has found that the ethanolic extract is toxic to rabbits by oral and intravenous routes. The bark and root are toxic to sheep and cattle. The poisonous principles were not identified.

The above compounds can be isolated from the plant by any suitable method, for example, by solvent extraction and chromatography, as illustrated in the Examples. In accordance with an embodiment of the invention, the isolated or purified compound has a purity of at least 50% or more, for example, 60% or more, 70% or more, 80% or more, 90% or more. For example, the isolated or purified compounds or epimers can have a purity of about 60% to 100%, preferably from about 80% to about 99%, and more preferably from about 90% to 100% by weight.

The compounds of formula I can be prepared by any suitable synthetic methodology. For example, in a hemisynthetic route, various ester groups [Ar—C($R^4$)-a-C($R^5$)—C(=O)—O—] can be placed on the guaiane derivative after hydrolysis of the naturally occurring ester groups. Esterification can be carried out on the hydroxyl group by methods known to those skilled in the art, for example, through the use of an acid chloride or acid anhydride and a suitable base. The desired ester moieties can be prepared from suitable cinnamoyl moieties. Halogenated englerins can be prepared by halogenating the isolated or purified englerins or during the isolation or purification.

Isolation and/or preparation of englerins and derivatives thereof are described in WO 2009/088854 A1 and WO 2011/120886 A1, the disclosures of which are incorporated herein in their entirety. WO '854 also discloses the utility of englerins and derivatives thereof as anticancer agents.

In accordance with an embodiment of the present invention, the disease or condition associated with insulin resistance is diabetes, obesity, inflammation, metabolic syndrome, polycystic ovary disease, arteriosclerosis, non-alcoholic fatty liver disease, reproductive abnormality in a female, and growth abnormality. In an embodiment, the disease associated with insulin resistance is type 1 and/or type 2 diabetes, particularly type 2 diabetes.

Polycystic ovary syndrome or disease is a condition in which there is an imbalance of a woman's female sex hormones. The hormone imbalance may cause changes in the menstrual cycle, e.g., absent periods or irregular menstrual periods, development of male sex characteristics, skin changes, e.g., acne or dark or thick skin markings around the armpits, groin, neck, and breasts, small cysts in the ovaries, trouble getting pregnant, and other problems.

Obesity relates to excess body fat. Obesity is associated with an increased incidence of diabetes, hypertension, increased levels of very low density lipoproteins (VLDL) triglycerides, low density lipoproteins (LDL) cholesterol, and decreased levels of high density lipoproteins (HDL) cholesterol, all of which are risk factors for the development of vascular disease. Obesity is also a known risk factor for non-alcoholic fatty liver disease, hypertension, stroke, gall bladder disease, osteoarthritis, obstructive sleep apnea and other breathing problems, as well as some forms of cancer In accordance with an embodiment of the invention, the treatment of arteriosclerosis includes delaying or preventing the development of coronary artery disease, stroke, or peripheral vascular disease. In accordance with an embodiment of the invention, the treatment of fatty liver includes delaying or preventing the progression of cirrhosis of the liver.

In accordance with embodiments, the present invention provides methods of treating, preventing, ameliorating, and/or inhibiting a condition associated with insulin resistance comprising administering a compound of formula (I) or a salt of epimer thereof.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the inventive methods can provide any amount of any level of treatment, prevention, amelioration, or inhibition of the disorder in a mammal. For example, a disorder, including symptoms or conditions thereof, may be reduced by, for example, 100%, 90%, 80%, 70%, 60%, 50%, 40%, 30%, 20%, or 10%. Furthermore, the treatment, prevention, amelioration, or inhibition provided by the inventive method can include treatment, prevention, amelioration, or inhibition of one or more conditions or symptoms of the disorder, e.g., cancer. Also, for purposes herein, "treatment," "prevention," "amelioration," or "inhibition" can encompass delaying the onset of the disorder, or a symptom or condition thereof.

In accordance with the invention, the term "animal" includes a mammal such as, without limitation, the order Rodentia, such as mice, and the order Lagomorpha, such as rabbits. It is preferred that the mammals are from the order Carnivora, including Felines (cats) and Canines (dogs). It is more preferred that the mammals are from the order Artiodactyla, including Bovines (cows) and Swine (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The compound (or epimer thereof) is administered in a dose sufficient to treat the cancer. Such doses are known in the art (see, for example, the *Physicians' Desk Reference* (2004)). The compounds can be administered using techniques such as those described in, for example, Wasserman et al., *Cancer,* 36, pp. 1258-1268 (1975) and *Physicians' Desk Reference,* 58th ed., Thomson PDR (2004).

Suitable doses and dosage regimens can be determined by conventional range-finding techniques known to those of ordinary skill in the art. Generally, treatment is initiated with smaller dosages that are less than the optimum dose of the compound of the present invention. Thereafter, the dosage is increased by small increments until the optimum effect under the circumstances is reached. The present method can involve the administration of about 0.1 µg to about 50 mg of at least one compound of the invention per kg body weight of the individual. For a 70 kg patient, dosages of from about 10 µg to about 200 mg of the compound of the invention would be more commonly used, depending on a patient's physiological response.

By way of example and not intending to limit the invention, the dose of the pharmaceutically active agent(s) described herein for methods of treating or preventing a disease or condition as described above can be about 0.001 to about 1 mg/kg body weight of the subject per day, for example, about 0.001 mg, 0.002 mg, 0.005 mg, 0.010 mg, 0.015 mg, 0.020 mg, 0.025 mg, 0.050 mg, 0.075 mg, 0.1 mg, 0.15 mg, 0.2 mg, 0.25 mg, 0.5 mg, 0.75 mg, or 1 mg/kg body weight per day. The dose of the pharmaceutically active agent(s) described herein for the described methods can be about 1 to about 1000 mg/kg body weight of the subject being treated per day, for example, about 1 mg, 2 mg, 5 mg, 10 mg, 15 mg, 0.020 mg, 25 mg, 50 mg, 75 mg, 100 mg, 150 mg, 200 mg, 250 mg, 500 mg, 750 mg, or 1000 mg/kg body weight per day.

The pharmaceutically acceptable carrier (or excipient) is preferably one that is chemically inert to the compound of the invention and one that has no detrimental side effects or toxicity under the conditions of use. Such pharmaceutically acceptable carriers preferably include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG 400/60% saline), and alcohol (e.g., 40% ethanol/60% water).

A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, interperitoneal, rectal, and vaginal administration are merely exemplary and are in no way limiting. The pharmaceutical compositions can be administered parenterally, e.g., intravenously, intraarterially, subcutaneously, intradermally, intrathecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5% or less to about 25% or more by weight of a compound of the invention in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Topical formulations, including those that are useful for transdermal drug release, are well known to those of skill in the art and are suitable in the context of the present invention for application to skin.

Formulations suitable for oral administration can consist of (a) liquid solutions, such as an effective amount of a compound of the invention dissolved in diluents, such as water, saline, or orange juice; (b) capsules, sachets, tablets, lozenges, and troches, each containing a pre-determined amount of the compound of the invention, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the compound ingredient in a flavor, usually sucrose and acacia or tragacanth, as well as pastilles comprising a compound of the invention in an inert base, such as gelatin and glycerin, or sucrose and acacia, emulsions, gels, and the like containing, in addition to the compound of the invention, such excipients as are known in the art.

An compound or epimer of the present invention, alone or in combination with other suitable components, can be made into aerosol formulations to be administered via inhalation. A compound or epimer of the invention is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

Additionally, the compound or epimer of the invention can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the compound ingredient, such carriers as are known in the art to be appropriate.

The concentration of the compound or epimer in the pharmaceutical formulations can vary, e.g., from less than about 1% to about 10%, to as much as 20% to 50% or more by weight, and can be selected primarily by fluid volumes, and viscosities, in accordance with the particular mode of administration selected.

Thus, a typical pharmaceutical composition for intravenous infusion could be made up to contain 250 ml of sterile Ringer's solution, and 100 mg of at least one compound of the invention. Actual methods for preparing parenterally administrable compounds of the invention will be known or apparent to those skilled in the art and are described in more detail in, for example, *Remington's Pharmaceutical Science* (17$^{th}$ ed., Mack Publishing Company, Easton, Pa., 1985).

It will be appreciated by one of ordinary skill in the art that, in addition to the aforedescribed pharmaceutical compositions, the compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., *Ann. Rev. Biophys. Bioeng.,* 9, 467 (1980) and U.S. Pat. Nos. 4,235,871, 4,501,728, 4,837,028, and 5,019,369.

The following example further illustrates the invention but, of course, should not be construed as in any way limiting its scope.

EXAMPLE

This example demonstrates some of the biological activities of a compound in accordance with an embodiment of the invention. This example also illustrates the experimental procedures employed in determining the biological activities.

Cell lines: Kidney cancer cell line 786-0 and prostate cancer cell line PC3 were cultured in Dulbecco's modified Eagle's medium High Glucose (DMEM; Cellgro for 786-0 or RPMI (PC3), and supplemented with 10% fetal calf serum (Gibco).

Reagents: Englerin A was generously given by the Molecular Targets Development Program (Center for Cancer Research, National Cancer Institute, Frederick, Md.). Complete mini-protease inhibitor cocktail tablets were purchased from Roche. The siRNA for PKC alpha and zeta were obtained from Origene. Purified HSF 1 was purchased from Assay Design.

Analysis of cell viability in vitro: Cell viability was assessed by manual counting or by MTT as previously described (Bortezomib (velcade) for multiple myeloma, *Med Lett Drugs Ther.* 45, 57-58 (2003) and Sourbier et al., The phosphoinositide 3-kinase/Akt pathway: a new target in human renal cell carcinoma therapy, *Cancer Res* 66, 5130-5142, 2010). Briefly, 50,000 cells were plated in regular media in 12-well plates and treated with EA before to assess cell viability by manual counting using a hemocytometer. Alternatively 10,000 cells were plated in 96-well plates and treated with EA before to assess cell viability by MTT assay.

Glucose uptake assay: Glucose uptake was measured using a fluorescent non-metabolizable d-glucose analog 2-[N-(7-nitrobenz-2-oxa-1,3-diazol-4-yl)amino]-2-deoxy-d-glucose (2-NBDG). Five thousands cells were plated in black-well 96-well plates. After treatment as indicated, cells were incubated for 20 minutes in KREB buffer containing 1 g/L glucose in presence or absence of 20 μM of 2-NBDG. Cells were then washed 3 times for 5 minutes with PBS to remove all residual extracellular 2-NBDG. The amount of 2-NBDG imported into the cells was measured by spectrophotometry at 488 nm.

Xenograft tumor studies: Animal experiments were done following the ethics rules of the National Cancer Institute for animal studies. Ten million 786-0 or 1 million PC3 cells were implanted subcutaneously into female Nu/Nu mice. After 1-4 weeks (depending on the cell line), the tumors reached an average volume of 100-150 mm$^3$. The mice were randomly separated in two groups with comparable tumor volumes and treated six times a week intra-peritoneally (i.p.) with either englerin A at 5 mg/kg or the vehicle (PBS/DMSO). Tumors were measured throughout the experiments using calipers and their volumes were estimated using the formula (L×W2)/2. At the end of the experiments, blood was collected, and tumors and organs were surgically excised and frozen or paraffin-embalmed for further analysis.

Figure 1A:
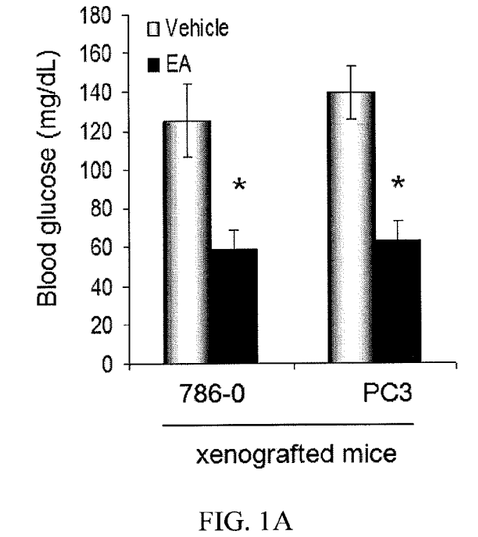
FIG. 1A depicts the blood glucose levels in the blood of xenografted mice treated with englerin A (represented as EA in the drawings). The mice were xenografted with 786-0 and PC3 cancer cells.

Blood glucose quantification: Thirty minutes after removing access to the food to the mice, their blood glucose was monitored 5 min post-injection of englerin A in i.p. (5 mg/kg), by the use of an OneTouch® UltraMini® glucose meter and OneTouch®Ultra strips (OneTouch®). The results obtained are shown in FIG. 1A.

Figure 1B:
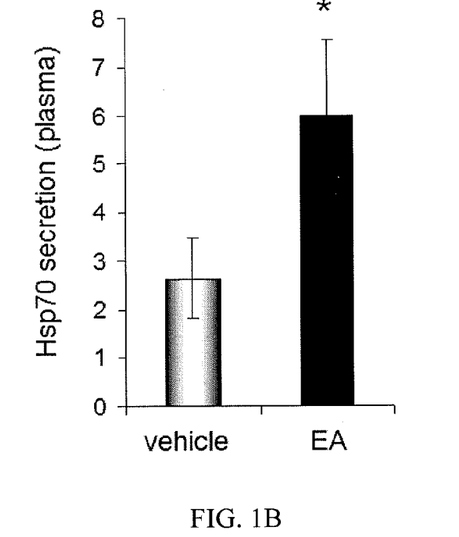
FIG. 1B depicts the HSP70 levels in the plasma of the xenografted mice and shows that englerin A significantly increases HSP70 level in the blood of the mice.
Figure 1C:
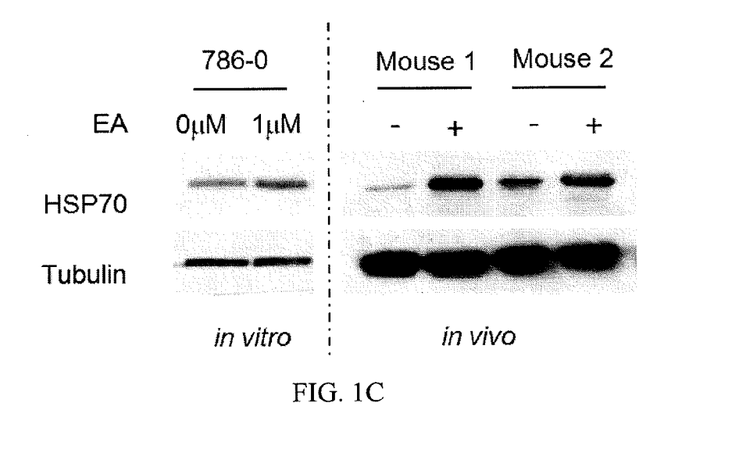
FIG. 1C depicts the Western blot of in vitro and in vivo levels of HSP70.

HSP70 secretion: HSP70 secretion in the plasma of tumor-bearing mice was assessed using an ELISA kit purchased from Assay Designs, Inc., and following the manufacturer's protocol. The blood of the mice was collected 4 hrs after intraperitoneal (i.p.) injection of englerin A or vehicle (PBS/DMSO). The results obtained are shown in FIG. 1B.

Figure 2:
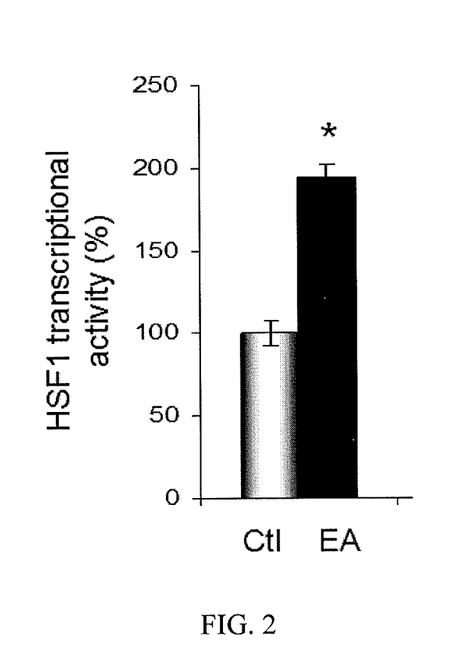
FIG. 2 depicts the in vitro HSF1 transcriptional activity induced by englerin A as determined by a reporter assay.

HSF 1 transcriptional activity: HSF 1 transcriptional activity assay was measured using a GFP-tag HSE promoter reporter assay from HSP70 gene (generously given by Dr Luke Whitesell, Harvard, MA). Cells were transfected with the reporter plasmid 24 h prior to the experiment. Cells were treated as described 4-6 h before to measure GFP emission by spectrophotometry. The results obtained are shown in FIG. 2A.

Nuclear translocation of HSF1 was visualized by immunofluorescence: 786-0 cells were plated in 2-wells chamber-slides and treated for 1 h with englerin A 1 μM before fixing it with 4% paraformaldehyde. Cells were then blocked 1 h with BSA 3% and permeabilized with Triton 0.5%. HSF1 antibody was incubated overnight at 4° C. in a wet atmosphere. After 3 washes with TBST buffer, the slides were incubated 1 h with a secondary antibody coupled to Alexa455, before being washed and mounted. DAPI (Cell Signaling Inc.) was used to stain the nucleus of the cells.

Pictures were taken using a confocal microscope Zeiss NLO510. The results obtained are shown in FIG. 2B.

HSF1 phosphorylation: Purified HSF1 was incubated with purified PKC-θ in presence of EA (1 µM) and radioactive ATP (10 µM) for 30 min at 30° C. Phosphorylation of HSF1 was assessed by radiocount. The results obtained are shown in FIG. 2B.

Statistics: Unless specified, all values are expressed as mean±Standard Error. Values were compared using the Student-Newman-Keul's test. P<0.05 was considered significant.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating an animal for insulin resistance or type II diabetes comprising administering to the animal an effective amount of a compound of formula (I):

or an epimer thereof; wherein

Ar is an aryl group, optionally substituted with one or more substituents selected from the group consisting of $C_1$-$C_6$ alkyl, $C_1$-$C_6$ hydroxyalkyl, $C_1$-$C_6$ alkoxy, halo, and nitro;

X is O;

$R^2$ and $R^3$ are independently $C_1$-$C_6$ alkyl;

$R^1$ is isopropyl;

"a" is a single bond or a double bond;

when "a" is a double bond, $R^4$ is hydrogen, and $R^5$ is halo or H;

when "a" is a single bond, $R^4$ is selected from the group consisting of halo, hydroxy, and $C_1$-$C_6$ alkoxy and $R^5$ is halo or H; and $R^6$ is H, $C_1$-$C_6$ alkyl carbonyl, or hydroxy $C_1$-$C_6$ alkyl carbonyl.

2. The method of claim 1, wherein the compound of formula (I) is Englerin A, which is of the formula:

3. The method of claim 1, wherein $R^6$ is hydroxy $C_1$-$C_6$ alkyl carbonyl or hydroxymethyl carbonyl.

4. The method of claim 1, wherein $R^5$ is halo.

5. The method of claim 4, wherein $R^5$ is chloro.

6. The method of claim 1, wherein Ar is phenyl, optionally substituted with one or more substituents substituent selected from the group consisting of $C_1$-$C_6$ alkyl, $C_1$-$C_6$ hydroxyalkyl, $C_1$-$C_6$ alkoxy, halo, and nitro.

7. The method of claim 1, wherein "a" is a double bond and the double bond is E, Z, or a mixture of E and Z.

8. The method of claim 1, wherein "a" is a single bond.

9. The method of claim 8, wherein $R^4$ is hydroxy, chloro, or ethoxy.

10. The method of claim 1, wherein $R^2$ and $R^3$ are methyl.

11. The method of claim 3, wherein the compound of formula (I) is:

2'-Chloroenglerin A

2'-Chloro,3'-hydroxydihydroenglerin A (epimer 1, 2, 3, or 4)

2',3'-Dichlorodihydroenglerin A (epimer 1 or 2)

2'-Chloro,3'-ethoxydihydroenglerin A wherein the double bond "a" in 2'-Chloroenglerin A can be E, Z, or E/Z.

12. The method of claim 1, wherein $R^6$ is $C_1$-$C_6$ alkyl carbonyl.

13. The method of claim 4, wherein $R^6$ is hydroxymethyl carbonyl.

* * * * *